United States Patent [19]
Schultz

[11] Patent Number: 5,897,528
[45] Date of Patent: Apr. 27, 1999

[54] FILTERED INTRACEREBROVENTRICULAR OR INTRASPINAL ACCESS PORT WITH DIRECT CEREBROSPINAL FLUID ACCESS

[75] Inventor: Brenda Kay Schultz, Minneapolis, Minn.

[73] Assignee: Medtronic, Inc., Minneapolis, Minn.

[21] Appl. No.: 09/070,248

[22] Filed: Apr. 30, 1998

[51] Int. Cl.⁶ .................................................. A61M 31/00

[52] U.S. Cl. ................................ 604/49; 604/93; 604/247

[58] Field of Search .................................. 604/49, 51, 93, 604/30, 246, 247

[56] References Cited

U.S. PATENT DOCUMENTS

| | | | |
|---|---|---|---|
| 4,781,680 | 11/1988 | Redmond et al. | 604/93 |
| 5,185,003 | 2/1993 | Brethauer | 604/93 |
| 5,695,490 | 12/1997 | Flaherty et al. | 604/891.1 |

OTHER PUBLICATIONS

James M. Fdrake, Christian Sainte–Rose, "The Shunt Book" (Figures 2–6 and 2–7) Blackwell Science, Inc., 1995.

*Primary Examiner*—Corrine McDermott
*Attorney, Agent, or Firm*—Curtis D. Kinghorn; Harold R. Patton

[57] ABSTRACT

An access port and method of use is described that has a filter assembly along a fluid flow path through the access port. The access port is in fluid communication with a catheter that is surgically implanted in a patient's brain or intraspinal space. The filter assembly has a filter element and a series of one-way valves. The one-way valves allow the fluid to flow easily across the filter assembly in one direction but prohibit fluid flow through the one-way valves in the opposite direction. The one-way valves are oriented to allow fluid flow from the catheter to a chamber within the access port which can be accessed by a needle. Drug or other medication to be administered to the patient through a needle must pass through the filter before entering catheter to be ultimately administered to the patient.

16 Claims, 6 Drawing Sheets

FILTERED INTRACEREBROVENTRICULAR OR INTRASPINAL ACCESS PORT WITH DIRECT CEREBROSPINAL FLUID ACCESS

BACKGROUND OF THE INVENTION

1. Field of the Invention

This invention relates generally to medical devices which are implantable in the human body and more particularly relates to a subcutaneously implantable direct delivery access port for delivering drugs to the ventricles of the brain or to the intraspinal area.

2. Description of Related Art

It is often desirable for a physician or other health care professional to withdraw cerebrospinal fluid (CSF) from a patient in order to assess the condition of the CSF or to administer drug to the CSF. Access ports, such as the model 8506 ICV Access Port and the 8507 Intraspinal Port, developed by Medtronic, Inc. of Minneapolis, Minn., allow the physician or other healthcare professional to intermittently withdraw CSF from the ventricles of a patient's brain or intraspinal space or administer drug to the CSF.

These access ports are typically placed cranially or over the ribs and are connected to a catheter which is surgically placed in the intraventricular space of the brain or intraspinal area of the spinal cord. CSF is withdrawn by inserting a needle through the patient's skin and through a septum that forms the top of the port. The end of the needle is located in the port and CSF is withdrawn from the patient through the catheter and port.

When it is desirable to administer drug to the CSF, a needle is inserted through the patient's skin, through the septum and into the port which is connected to a catheter. The drug is passed into the port where it passes through the catheter into the patient's CSF.

SUMMARY OF THE INVENTION

An access port is described that has a filter assembly along a fluid flow path through the access port. The access port is in fluid communication with a catheter that is surgically implanted in a patient's brain or intraspinal space. The filter assembly has a filter element and a series of one-way valves. The one-way valves allow the fluid to flow easily across the filter assembly in one direction but prohibit fluid flow through the one-way valves in the opposite direction. The one-way valves are oriented to allow fluid flow from the catheter to a chamber within the access port which can be accessed by a needle.

In operation, when it is desirable to remove CSF from a patient, a needle is inserted into the access port. Fluid is withdrawn from within the access port. As fluid is withdrawn, CSF passes through the one-way valves to the chamber where it is removed through the needle. Because the CSF passes through the one-way valves, the CSF removed from the access port is not filtered by passing through the filter.

To add drug or other medication to the CSF, the drug is introduced under pressure into the chamber within the access port. The pressure on the drug causes the drug to contact the filter assembly. At the filter assembly, because the one-way valves are biased to prohibit fluid flow toward the catheter, the drug must pass through the filter before passing to the catheter and on to the patient's ventricle. In this way, the drug passing to the ventricle is filtered to remove particulate, bacteria or other undesirable contaminants.

DETAILED DESCRIPTION OF THE INVENTION

Figure 1:
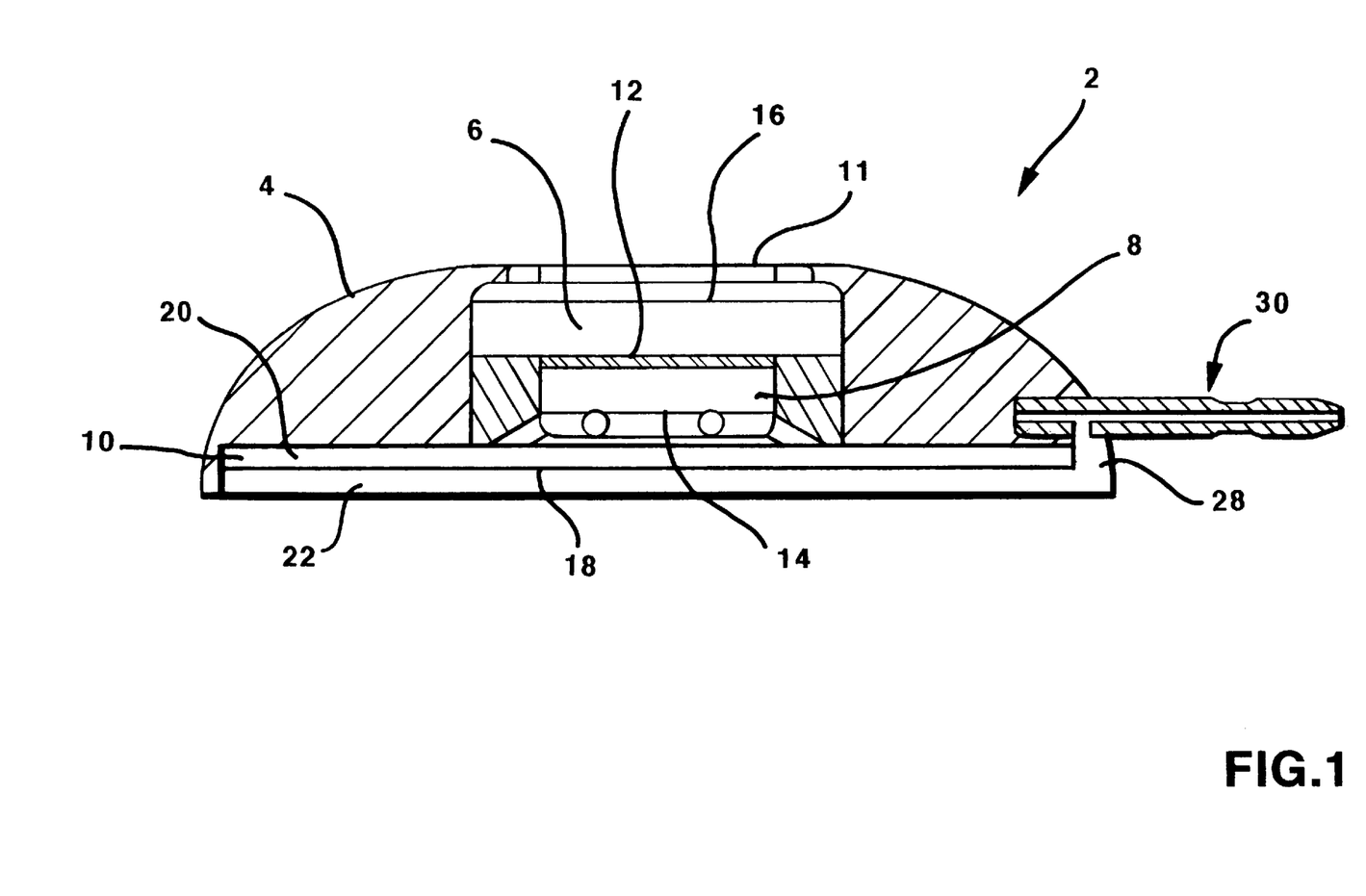
FIG. 1 is a cross-section side view of the access port of the present invention.
Figure 2:
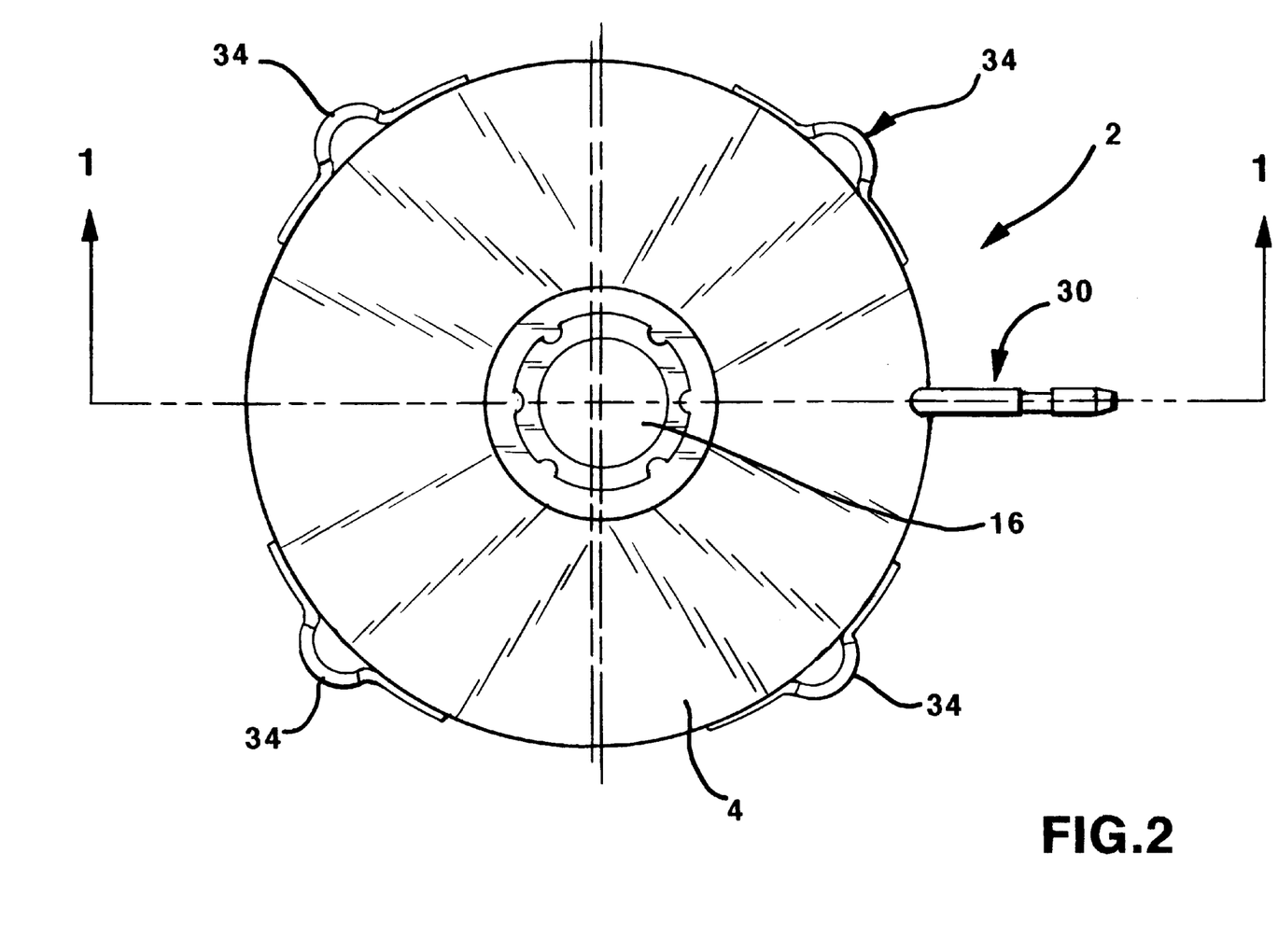
FIG. 2 is a top view of the access port of the present invention.

An access port according to the present invention is shown in FIGS. 1 and 2 generally labeled 2. The access port 2 includes a generally disk shaped housing 4. Housing 4 has a centrally located cylindrical upper cavity 6, a middle cavity 8 and a lower cavity 10. In the preferred embodiment, upper cavity 6, middle cavity 8 and lower cavity 10 are generally cylindrical. Upper cavity 6 extends from the upper surface 11 of housing 4 into housing 4 and terminates at the upper/middle boundary surface 12 of upper cavity 6 and middle cavity 8. Middle cavity 8 extends between upper cavity 6 and lower cavity 10, being defined at its upper boundary by upper/middle boundary surface 12 and at its lower boundary by middle/lower boundary surface 14. Lower cavity 10 is preferably wider and has less height than either upper cavity 6 or middle cavity 8.

It is clear that upper cavity 6 and middle cavity 8 could be replaced with a single cavity. In addition, upper cavity 6, middle cavity 8 and lower cavity 10 may each or all be non-cylindrical. Further, although the preferred embodiment has upper cavity 6, middle cavity 8 and lower cavity 10 located along a central axis of housing 4, upper cavity 6, middle cavity 8 and lower cavity 10 may be located offset from a central axis of housing 4 or in addition or in the alternative, be located offset from each other so long as they are in fluid communication with each other.

Upper cavity 6 contains a septum 16 that fills upper cavity 6 by extending from near the upper surface 11 of housing 4 into upper cavity 6. Septum 16 closes the upper end of upper cavity 6. Septum 16 is preferably made of a pliable elastomeric material. Septum 16 provides a resealable passage for a needle as will be explained hereafter.

Figure 5:
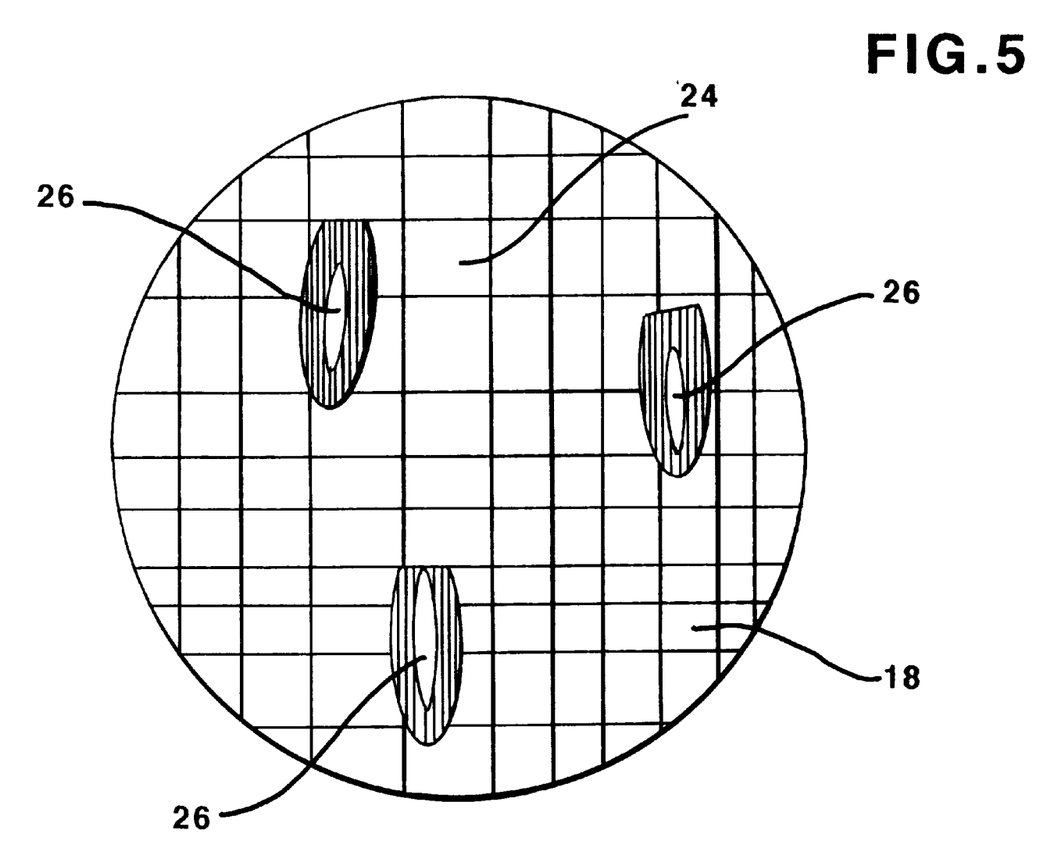
FIG. 5 shows a top view of one portion of one embodiment of the filter assembly of the present invention.

A filter assembly 18 extends entirely across the middle of lower cavity 10. Filter assembly 18 separates lower cavity 10 into an upper filter chamber 20 and a lower filter chamber 22. As shown in FIG. 5, filter assembly 18 has two parts, a 0.22 micron filter 24 and a series of one-way valves 26. Filter 24 allows fluid and particles smaller than 0.22 micron to pass through filter 24 while one-way valves 26 allow fluid to pass only from lower filter chamber 22 to upper filter chamber 20. The significance of filter 24 being 0.22 micron is that this is the size filter that is generally believed to be effective in filtering bacteria and other similar particles. While a filter 24 having a pore size of 0.22 micron is preferred, any filter having any pore size is within the scope of the invention, the key idea being that fluid is filtered by passing through filter 24 as desired. In particular, it is within the scope of the invention to have a filter 24 with a pore size of from about 0.22 microns to about 0.44 microns.

Figure 3A:
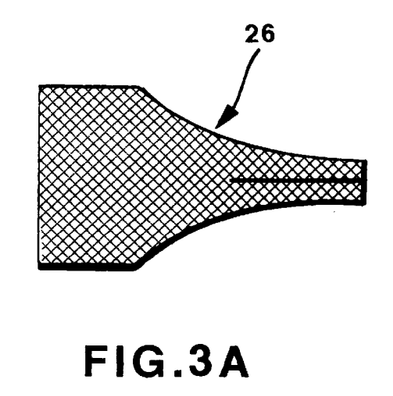
FIG. 3A is a side view of a closed miter valve of the present invention.
Figure 3B:
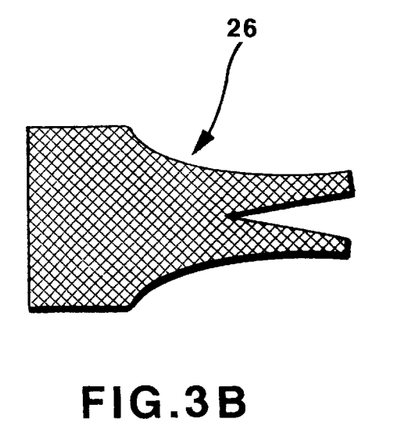
FIG. 3B is a side view of an open miter valve of the present invention.
Figure 4A:
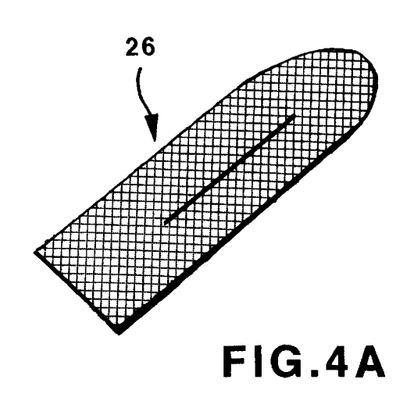
FIG. 4A is a side view of a closed slit valve of the present invention.
Figure 4B:
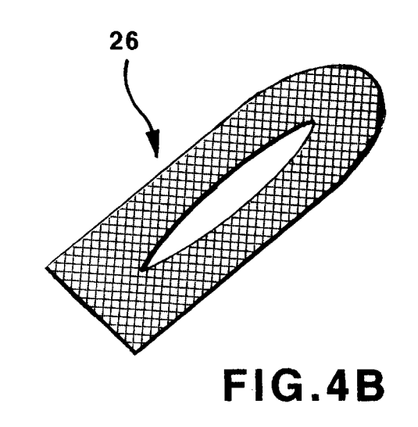
FIG. 4B is a side view of an open slit valve of the present invention.

One-way valves 26 may preferably be a miter valve as shown in the closed and open configuration, respectively, in FIGS. 3A and 3B. Alternately, one-way valves 26 may be slit valves such as those shown in the closed and open configuration, respectively, in FIGS. 4A and 4B. In either embodiment, one-way valves 26 are dispersed across the filter assembly 18 as shown in FIG. 5.

A passage 28 connects lower filter chamber 22 to a connector 30. Connector 30 preferably is a tubular connector that a catheter 32 is placed over and in mating contact with. This allows catheter 32 to be fluidly connected to access port 2.

Access port 2 also includes a series of suture loops 34 attached to the outer periphery of housing 4. Suture loops 34 allow access port 2 to be secured in place cranially.

Figure 6:
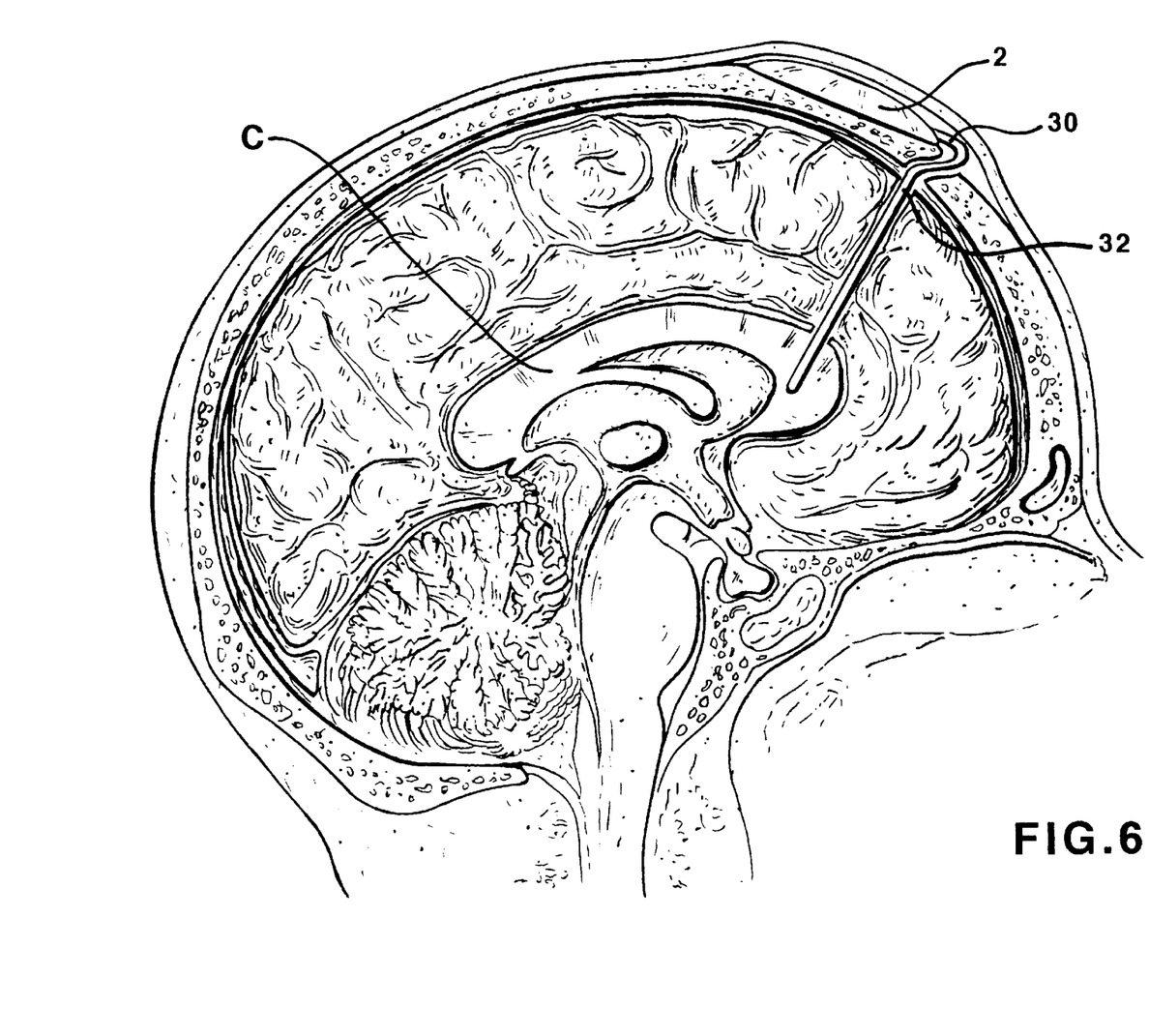
FIG. 6 is a side cross-sectional view of the access port of the present invention in place on a human head and attached to a catheter that is implanted in the ventricle of the brain.
Figure 7:
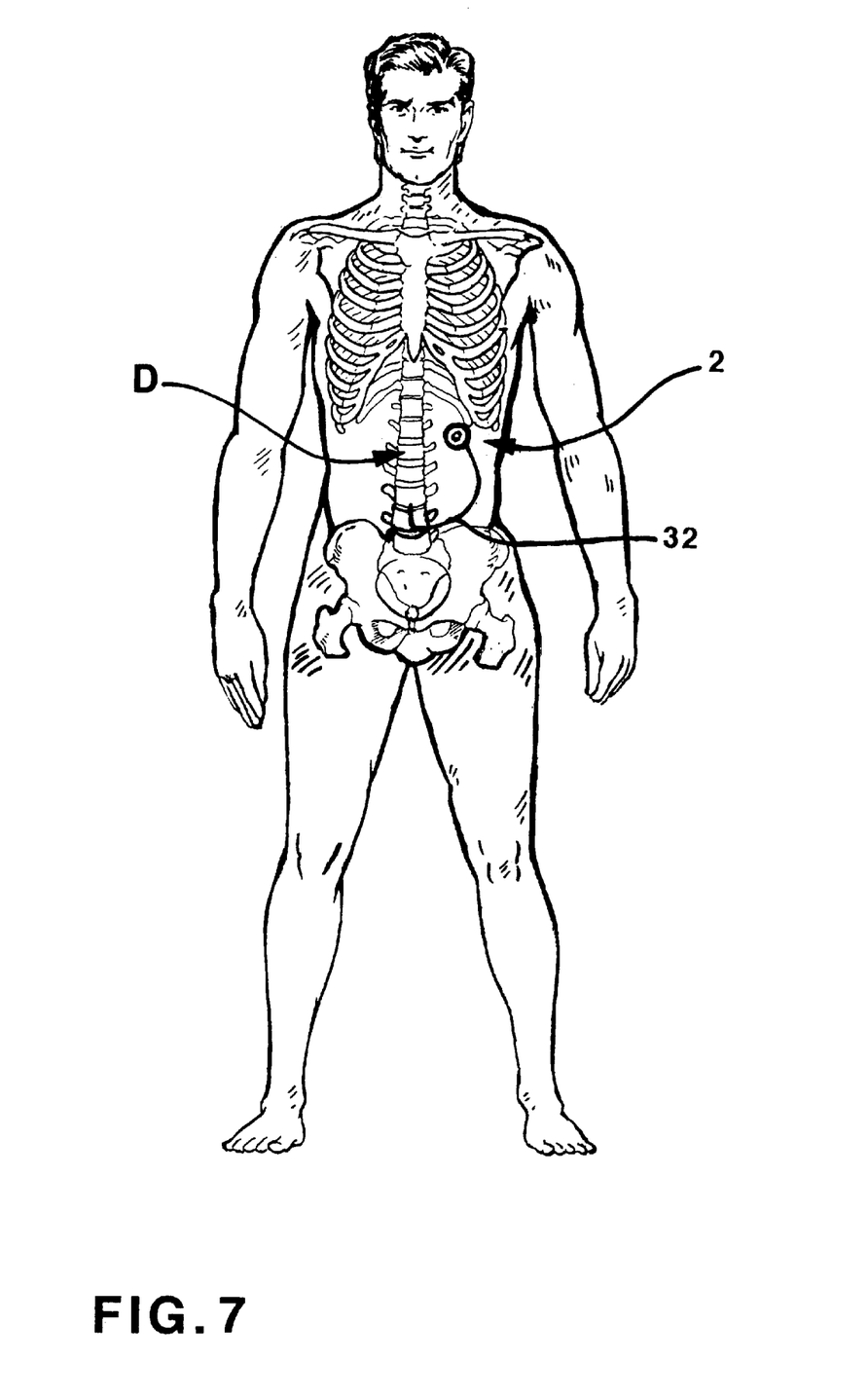
FIG. 7 is a side cross-sectional view of the access port of the present invention in place on a human rib-cage and attached to a catheter that is implanted in the intraspinal space.

In a ventricular placement of the access port 2, a catheter 32 is surgically placed in a patient's ventricle. Access port 2 is placed cranially as shown in FIG. 6 and sutures are placed through suture loops 34 to hold access port 2 in place. In an intraspinal placement of the access port 2, a catheter 32 is surgically placed in an intraspinal space. Access port 2 is placed over the rib cage as shown in FIG. 7. The natural pressure of CSF within the body will cause CSF to move through catheter 32 into lower filter chamber 22. This natural pressure will cause CSF to seep through one-way valves 26 into upper filter chamber 20 and upper cavity 6 below septum 16.

To remove CSF, a needle attached to a syringe is placed through septum 16 so that the end of the needle is in upper cavity 6 below septum 16. The syringe plunger is withdrawn to remove CSF from the upper cavity 6 through the needle. As CSF is removed from upper cavity 6, new CSF is pulled through catheter 32, into lower filter chamber 22, through one-way valves 26, into upper filter chamber 20 and into upper cavity 6. Because the CSF passes through one-way valves 26, which are relatively easier to pass through than filter 24, the CSF does not pass through filter 24. As a result, the CSF removed from the access port 2 is unfiltered so that the physician or other health care professional will be able to accurately assess the true state of the CSF.

To add drug or other medicament to the CSF, a needle attached to a syringe is placed through septum 16 so that the end of the needle is in upper cavity 6 below septum 16. The syringe is activated to push the drug into the upper cavity 6 through the needle. As drug is introduced into upper cavity 6, the drug passes into upper filter chamber 20 where it encounters filter assembly 18. Because one-way valves 26 are biased to not allow fluid to pass from upper filter chamber 20 to lower filter chamber 22, the drug must pass through filter 24 to pass from upper filter chamber 20 to lower filter chamber 22. The drug then passes through passage 28 and catheter 32 to the patient's ventricle.

The invention has been described in connection with a particular embodiment. It is to be understood that the description given herein has been given for the purpose of illustrating the invention and the specific details of the invention given herein are not intended to limit the invention. It is clear that improvements and modifications to the description given herein will occur to those skilled in the art and will still fall within the scope of the following claims.

What is claimed is:

1. A method of withdrawing unfiltered cerebrospinal fluid from a patient comprising the steps of:

placing a catheter in the patient's ventricle;

placing an access port cranially, the access port having:

a housing having an upper surface, an upper cavity and a lower cavity, the upper cavity extending from the upper surface of housing into the housing and terminating at the lower cavity;

a septum located in the upper cavity;

a filter assembly extending entirely across the lower cavity separating the lower cavity into an upper filter chamber in fluid commnunication with the upper cavity and a lower filter chamber, the filter assembly having a filter part and at least one one-way valve, the one way valve oriented to allow fluid to pass only from the lower filter chamber to the upper filter chamber;

an outlet port in fluid communication with the lower filter chamber;

connecting said catheter to said outlet port;

allowing cerebrospinal fluid to move through the catheter into the lower filter chamber, through the one-way valve into the upper filter chamber and the upper cavity whereby unfiltered cerebrospinal fluid is introduced into the upper cavity;

placing a needle attached to a syringe through the septum into the upper cavity;

drawing unfiltered cerebrospinal fluid through the needle.

2. A method of administering fluid to the ventricle of a patient comprising the steps of:

placing a catheter in the patient's ventricle;

placing an access port cranially, the access port having:

a housing having an upper surface, an upper cavity and a lower cavity, the upper cavity extending from the upper surface of housing into the housing and terminating at the lower cavity;

a septum located in the upper cavity;

a filter assembly extending entirely across the lower cavity separating the lower cavity into an upper filter chamber in fluid communication with the upper cavity and a lower filter chamber, the filter assembly having a filter part and at least one one-way valve, the one way valve oriented to allow fluid to pass only from the lower filter chamber to the upper filter chamber;

an outlet port in fluid communication with the lower filter chamber;

connecting said catheter to said outlet port;

placing a needle attached to a syringe through the septum into the upper cavity;

administering the fluid from the needle into the upper cavity wherein the fluid passes into the upper filter chamber, across the filter part, into the lower filter chamber, through the port and into the patient's ventricle.

3. A method of withdrawing unfiltered cerebrospinal fluid from a patient comprising the steps of:

placing a catheter in the patient's intraspinal space;

placing an access port over the patient's rib cage, the access port having:

a housing having an upper surface, an upper cavity and a lower cavity, the upper cavity extending from the upper surface of housing into the housing and terminating at the lower cavity;

a septum located in the upper cavity;

a filter assembly extending entirely across the lower cavity separating the lower cavity into an upper filter chamber in fluid communication with the upper cavity and a lower filter chamber, the filter assembly having a filter part and at least one one-way valve, the one way valve oriented to allow fluid to pass only from the lower filter chamber to the upper filter chamber;

an outlet port in fluid communication with the lower filter chamber;

connecting said catheter to said outlet port;

allowing cerebrospinal fluid to move through the catheter into the lower filter chamber, through the one-way valve into the upper filter chamber and the upper cavity whereby unfiltered cerebrospinal fluid is introduced into the upper cavity;

placing a needle attached to a syringe through the septum into the upper cavity;

drawing unfiltered cerebrospinal fluid through the needle.

4. A method of administering fluid to the ventricle of a patient comprising the steps of:

placing a catheter in the patient's intraspinal space;

placing an access port over the patient's rib cage, the access port having:

a housing having an upper surface, an upper cavity and a lower cavity, the upper cavity extending from the upper surface of housing into the housing and terminating at the lower cavity;

a septum located in the upper cavity;

a filter assembly extending entirely across the lower cavity separating the lower cavity into an upper filter chamber in fluid communication with the upper cavity and a lower filter chamber, the filter assembly having a filter part and at least one one-way valve, the one way valve oriented to allow fluid to pass only from the lower filter chamber to the upper filter chamber;

an outlet port in fluid communication with the lower filter chamber;

connecting said catheter to said outlet port;

placing a needle attached to a syringe through the septum into the upper cavity;

administering the fluid from the needle into the upper cavity wherein the fluid passes into the upper filter chamber, across the filter part, into the lower filter chamber, through the outlet port and catheter into the patient's ventricle.

5. An access port comprising:

a housing having an upper surface, an upper cavity and a lower cavity, the upper cavity extending from the upper surface of housing into the housing and terminating at the lower cavity;

a septum located in the upper cavity;

a filter assembly extending entirely across the lower cavity separating the lower cavity into an upper filter chamber in fluid communication with the upper cavity and a lower filter chamber, the filter assembly having a filter part and at least one one-way valve, the one way valve oriented to allow fluid to pass only from the lower filter chamber to the upper filter chamber;

an outlet port in fluid communication with the lower filter chamber.

6. The access port of claim 5 wherein the upper cavity has a middle cavity located between the upper surface and the lower cavity.

7. The access port of claim 5 wherein the upper cavity is generally cylindrical.

8. The access port of claim 5 wherein the lower cavity is generally cylindrical.

9. The access port of claim 5 wherein the housing is generally disk shaped.

10. The access port of claim 5 wherein the filter has a pore size of about 0.22 micron.

11. The access port of claim 5 wherein the one-way valve is a miter valve.

12. The access port of claim 5 wherein the one-way valve is a slit valve.

13. The access port of claim 5 wherein the filter assembly includes at least two one-way valves.

14. The access port of claim 13 wherein the at least two one-way valves are dispersed over the filter assembly.

15. The access port of claim 5 further comprising a passage connecting the lower filter chamber to the out port.

16. The access port of claim 5 further comprising at least one suture loop attached to said housing.

* * * * *

UNITED STATES PATENT AND TRADEMARK OFFICE
CERTIFICATE OF CORRECTION

PATENT NO. : 5,897,528
DATED : April 27, 1999
INVENTOR(S) : Brenda K. Schultz

It is certified that error appears in the above-identified patent and that said Letters Patent is hereby corrected as shown below:

Column 6, line 42, "out port" should be "outlet port"

Signed and Sealed this

Twentieth Day of June, 2000

Attest:

Q. TODD DICKINSON

*Attesting Officer*      *Director of Patents and Trademarks*